United States Patent [19]

Barth

[11] 4,249,414

[45] Feb. 10, 1981

[54] APPARATUS FOR TESTING HARDNESS OF WOODEN POLES

[75] Inventor: Leonard A. Barth, Pte. Claire, Canada

[73] Assignee: Northern Telecom Limited, Montreal, Canada

[21] Appl. No.: 102,243

[22] Filed: Dec. 10, 1979

[51] Int. Cl.³ ............................................. G01N 3/42
[52] U.S. Cl. ........................................... 73/81; 73/85
[58] Field of Search ....................................... 73/81, 85

[56] References Cited

U.S. PATENT DOCUMENTS

| | | | |
|---|---|---|---|
| 3,308,654 | 3/1967 | Badgley | 73/81 |
| 3,618,369 | 11/1971 | Hamilton et al. | 73/81 |
| 3,934,463 | 1/1976 | Vendergagt | 73/81 |
| 4,118,975 | 10/1978 | Iwasaki | 73/81 |
| 4,196,616 | 4/1980 | Argabrite et al. | 73/81 |

FOREIGN PATENT DOCUMENTS

| | | | |
|---|---|---|---|
| 2228415 | 12/1972 | Fed. Rep. of Germany | 73/81 |
| 593112 | 2/1978 | U.S.S.R. | 73/81 |

OTHER PUBLICATIONS

Publ. "Is Wood Hardness Affected by Preservative Treatment" R. L. Ethington, pp. 60-61, vol. 22, No. 5, (SD 1 F56) Forest Products Journal, May 1972.

Primary Examiner—Daniel M. Yasich
Attorney, Agent, or Firm—John E. Mowle

[57] ABSTRACT

A method and apparatus for testing the hardness of wooden telephone and powerline poles to determine whether they are safe for climbing by linemen. A gaff is wedged into the side of the pole a preselected distance under hydraulic pressure. The maximum applied pressure is a measure of the hardness of the wood which correlates well with the results obtained during subjective tests by linemen.

7 Claims, 1 Drawing Figure

U.S. Patent     Feb. 10, 1981     4,249,414
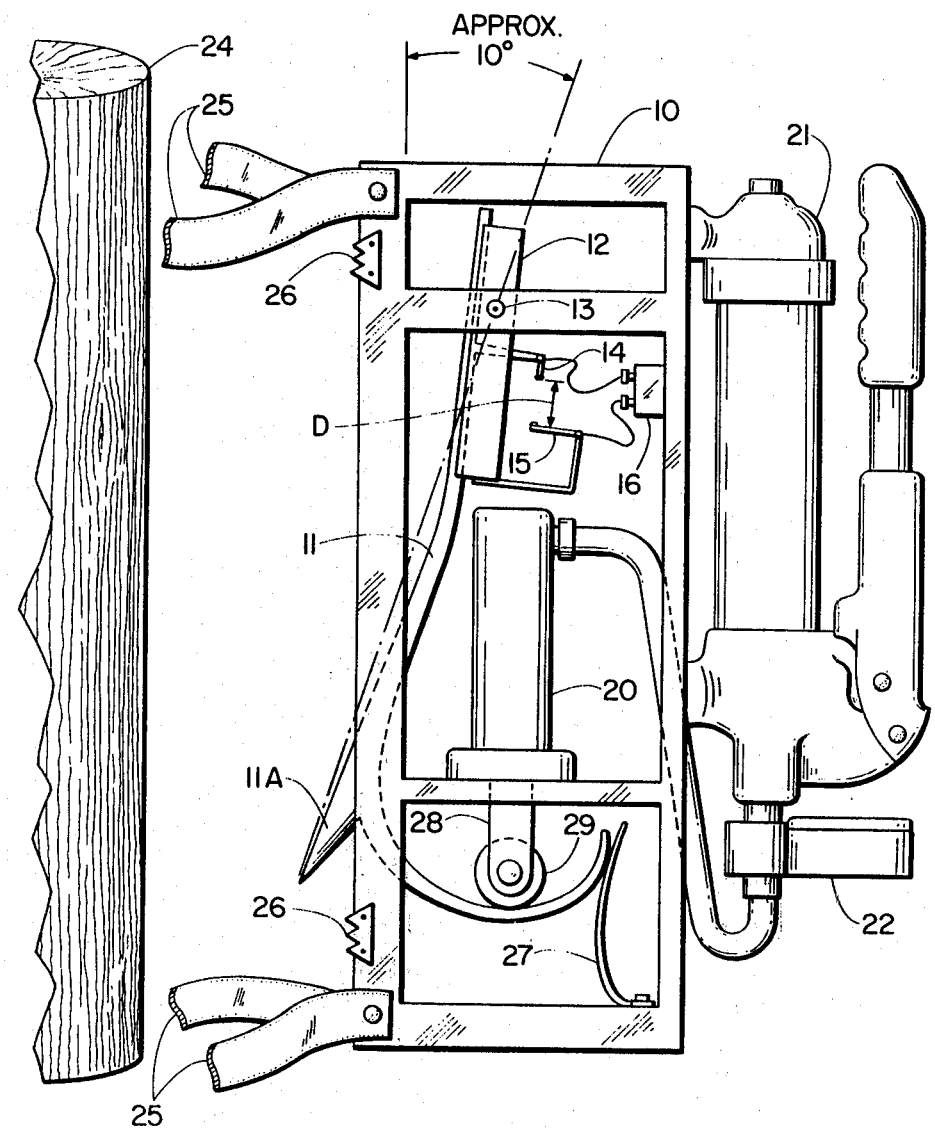

APPARATUS FOR TESTING HARDNESS OF WOODEN POLES

This invention relates to a method and apparatus for testing the hardness of the outer wood of a pole, and in particular one which may be used for testing treated poles used for carrying telephone and power lines.

BACKGROUND OF THE INVENTION

In recent years, various preservatives such as croesote, penta-petroleum and cromated copper arsenate, have been used to treat wooden poles so as to retard deterioration. Some of the preservatives appear to have a varying effect upon the hardness of the outer wood of the pole which can affect the safety of a lineman attempting to climb it. Too hard a wood can result in insufficient penetration of the lineman's gaff or spur into the side of the pole so that his foot may tear away the wood when he places his whole weight on it.

Various methods have been used in the past to test the hardness of this outer wood. For instance, a May 1972 article entitled "Is Wood Hardness Affected by Preservative Treatment?" by Robert L. Ethington, Forest Products Journal, Volume 22, No. 5, pages 60–61; describes the use of a standard ball hardness penetration test to check a number of poles treated with various preservatives. However, this test has been found to be relatively unsatisfactory in providing correlated results obtained in subjective field tests by linemen climbing the poles.

An earlier method is described in the Sept. 15, 1957 issue of Electric Light and Power in an article entitled "Treated-Pole Hardness Tested" by Henry A. Huber. Here, a conical spur is dropped down a tube mounted on the side of a standing pole at the same angle as a lineman's spur or gaff. The conical tip of the spur is graduated so that the amount of penetration into the wood can be read directly thereoff. However, a serious limitation of this device is that the tip of the spur causes a curled shaving of wood to form at the point of entry of the spur so that it is difficult to obtain an accurate reading on the amount of penetration. In addition, it cannot be readily used for checking poles during acceptance when they are lying flat on the ground.

STATEMENT OF THE INVENTION

The disadvantage of these prior arrangements have been overcome by the present invention of a hardness tester for wooden poles and the like which comprises means for applying a substantially steadily increasing pressure to a gaff to gradually force it into a side of a wooden pole. In addition, the tester includes a means for monitoring when the gaff has penetrated the pole a preselected distance and a means for monitoring the maximum applied pressure whereby the maximum pressure is a measure of the hardness of the outer wood of the pole.

In a particular embodiment, the tester includes a frame for mounting on the side of the pole. A gaff is slidably mounted on the frame with separate means so that its longitudinal direction of movement is freely alterable relative to the longitudinal axis of the pole. In addition, the tester includes means for urging the tip of the gaff against the side of the pole so that the longitudinal direction of movement is initially at a preset angle relative to the axis of the pole. In this embodiment the means for applying a substantially steadily increasing pressure is a hydraulic pump which includes a manometer. In a particular embodiment, the slidable axis of the gaff relative to the axis of the pole is less than about 25° and is preferably about 10° in order to substantially duplicate the angle of penetration of a lineman's gaff during actual use. The indicating means may include electrical contacts actuated by movement of the gaff with an electrical circuit responsive to actuation of the contacts for providing a suitable audio or visual signal.

It has been found there is high correlation between the test results using this method and apparatus and the observations of linemen under subjective tests using various types of wood treated with different chemicals under varying conditions.

DESCRIPTION OF THE DRAWINGS

An example embodiment of the invention will now be described with reference to the accompanying drawing which illustrates a hardness tester for wooden poles.

DESCRIPTION OF THE PREFERRED EMBODIMENT

Referring to the single FIGURE, the hardness tester comprises a frame 10 on which a gaff 11 is pivotally and slidably mounted. The upper portion of the gaff 11 is slidably mounted on a track 12 so that it can move up and down with minimal friction. In turn, the track 12 is pivotably mounted through a pin 13 on the frame 10 to enable the tip 11A of the gaff 11 to swing freely. Electrical contacts 14 and 15 connected to the gaff 11 and the track 12 respectively, are used to actuate an electrical buzzer 16 upon closure thereof to indicate that the gaff 11 has penetrated a preselected distance into the object under test.

Pressure is applied to the gaff 11 by a hydraulic cylinder 20 which is driven by a hydraulic pump 21 that includes a manometer 22 for monitoring the hydraulic pressure applied to the cylinder 20. The balance of the elements will be manifested from the following description of the function and operation of the tester.

During hardness testing of the outer wood of a pole or other similar object, the frame 10 is first secured to a pole 24 via straps 25. The tester will work equally well in any position so that the poles 24 may be tested before installation when lying horizontally, or after installation when standing vertically. Teeth 26, which dig into the side of the pole 24, are used to prevent movement of the frame 10 relative to the pole 24 during testing.

After securing the frame 10 to the pole 24, the tip 11A of the gaff 11 is urged against the side of the pole 24 and prevented from dropping due to gravity by a leaf spring 27. Upon actuation of the pump 21, a piston 28 in the cylinder 20 commences to force the tip 11A of the gaff 11 downward (as shown in the drawing) and into the side of the pole 24. Since the gaff 11 is free to pivot about the pin 13 it moves downward and inward at an angle of approximately 10° relative to the longitudinal axis of the wooden pole 24. A roller bearing 29 on the foot of the piston 28 minimizes lateral friction between it and the gaff 11. As the pump 21 is operated, the hydraulic pressure increases and the gaff 11 is steadily wedged into the side of the pole 24 in a controlled manner. By minimizing longitudinal and rotational friction, there is very little lateral pressure on the gaff during penetration. This helps to insure a high degree of repeatability of the results obtained during operation of the tester.

After the tip 11A of the gaff 11 has penetrated a preselected distance D of about 2.5 cm into the wood, contacts 14 and 15 close, thereby actuating the buzzer 16. At this point, the pressure on the manometer 22 is read and is a measure of the hardness of the outer wood of the pole 24. To ensure that a relatively soft or hard spot has not been selected, the test may be repeated several times. In practise, it has been found that only two readings need be taken if the results coincide, for a high degree of reliability.

In the illustrated embodiment, a standard lineman's gaff 11 which has been slightly modified so that it could be mounted in the tester, was used to penetrate the wood. However, other spur-like pieces could be used with equally reliable results. Since the test is primarily designed to simulate actual working conditions, the angle which the tip of the gaff 11 makes with the side of the pole should preferably simulate that of a lineman's spur. In practise, it has been found that an angle of only a few degrees normally between 10° and 15° and not more than about 20° provides excellent results.

The spring 27 which is used to urge the tip 11A of the gaff 11 against the side of the pole 24 need only be strong enough to initiate penetration of the gaff into the pole 24. The tip 11A is shaped so that it will normally chisel or wedge itself into the side of the pole 24 due to the downward thrust provided by piston 28 of the hydraulic cylinder 20. The 2.5 cm distance D is also somewhat arbitrary and was selected as approximately simulating the amount of penetration into the wood by a typical lineman's spur under normal working conditions. While penetrations of up to 6 cm can be readily used, it has been found that a high degree of repeatability can be obtained with penetrations as low as 2 cm. Much less than that might result in inconsistant readings due to surface defects in the wood.

In actual tests following a pole testing program using poles from several different types of trees, each treated with several different preservatives and containing various moisture contents, a high degree of correlation was obtained in virtually all cases with the subjective results obtained by several linemen during actual field trials. Thus, the tester can be confidentally used to pretest poles treated with various chemicals either before their acceptance or after their installation.

What is claimed is:

1. A hardness tester for wooden poles and the like comprising:
   a frame removably mountable on the side of a wooden pole;
   a gaff slidably mounted on the frame with separate means so that its longitudinal direction of movement freely alterable relative to the longitudinal axis of the pole;
   means for urging the tip of the gaff against the side of the pole so that the initial longitudinal direction of movement is at a preset angle relative to the axis of the pole;
   a hydraulic pump for applying a substantially steadily increasing pressure to the gaff to wedge the tip into the pole;
   a manometer for indicating the hydraulic pressure from the pump; and
   means for indicating when the tip has penetrated a preselected distance into the pole;
   whereby the indicated pressure at the preselected distance of penetration is a measure of the hardness of the outer wood of the pole.

2. A hardness tester as defined in claim 1, in which the initial longitudinal direction of movement of the gaff relative to the axis of the pole is about 10°.

3. A hardness tester as defined in claim 1, in which the longitudinal direction of movement of the gaff relative to said axis of the pole is less than about 25°.

4. A hardness tester as defined in claim 3, in which the indicating means includes electrical contacts actuated by movement of the gaff, and an electrical circuit responsive to actuation of the contacts for providing a signal to indicate that the tip has penetrated the preselected distance into the pole.

5. A hardness tester as defined in claim 4, in which the preselected distance of penetration of the gaff is between about 2 cm and 6 cm.

6. A hardness tester as defined in claim 5, in which the preselected distance of penetration of the gaff is about 2.5 cm.

7. A hardness tester for wooden poles and the like comprising:
   means for selectively applying increasing pressure to a gaff to wedge said gaff into a wooden pole;
   means for monitoring when the gaff has penetrated the pole a preselected distance;
   means for monitoring the maximum pressure applied to the gaff, said maximum pressure being a measure of the hardness of the outer wood of the pole;
   said hardness tester characterized by:
   the gaff being slidably mounted with separate means so that during testing its longitudinal direction of movement is freely alterable relative to the longitudinal axis of the pole; and
   means for urging the tip of the gaff against the side of the pole so that the initial longitudinal direction of movement is at a preset angle relative to the axis of the pole.

* * * * *